United States Patent [19]

November et al.

[11] Patent Number: 4,732,657
[45] Date of Patent: Mar. 22, 1988

[54] GEL-SLAB PLATE ASSEMBLY

[75] Inventors: Daniel November; Edmund R. Goldberg, both of New York, N.Y.

[73] Assignee: Haake-Buchler Instruments, Inc., Saddle Brook, N.J.

[21] Appl. No.: 64,558

[22] Filed: Jun. 22, 1987

[51] Int. Cl.[4] ...................... G01N 27/28; G01N 27/26
[52] U.S. Cl. ................................ 204/299 R; 204/182.8
[58] Field of Search .............. 204/182.8, 182.9, 299 R

[56] References Cited

U.S. PATENT DOCUMENTS

| | | | |
|---|---|---|---|
| 3,980,540 | 9/1976 | Hoefer ............................... | 204/182.8 |
| 4,142,960 | 3/1979 | Hahn et al. ...................... | 204/299 R |
| 4,290,871 | 9/1981 | Hoefer et al. ................... | 204/182.8 |
| 4,518,476 | 5/1985 | Delony et al. ................... | 204/299 R |
| 4,622,123 | 11/1986 | Nejame, Jr. ...................... | 204/299 R |

Primary Examiner—John F. Niebling
Assistant Examiner—John S. Starsiak, Jr.
Attorney, Agent, or Firm—Melvin K. Silverman

[57] ABSTRACT

Disclosed is an end clamp for use with a gel slab plate assembly, such assembly including a pair of flat, rectilinear plates separated at their longitudinal end surfaces by a resilient spacer. The end clamp includes an elongate wedge element having a longitudinal dimension substantially equal to the longitudinal dimension of said pair of flat plates. The wedge, in transverse cross-section, substantially defines a scalene triangle having a major base, a minor base and a hypotenuse. Said major base is adapted for flush press-fit contact with a flat end of said pair of rectilinear plates. Further provided is a substantially U-shaped clamp housing proportioned to longitudinally surround, on three sides, one longitudinal edge of the pair of plates. The clamp housing is provided, upon its plate-edge surrounding surface, with an inclined plane proportioned to mate with the hypotenuse of the wedge element. Further provided is a sub-assembly for selectively moving the hypotenuse of the wedge element along the inclined plane of the clamp housing. This includes a knob and threaded post for mechanically coupling the wedge through its minor base, to the clamp housing through an analog range of linear motion including, at one boundary condition thereof, a press-fit flush contact of the major base against the longitudinal end of the pair of plates. Thus, a uniform pressure of the major base of the wedge element against the plate edge may be obtained.

2 Claims, 3 Drawing Figures

GEL-SLAB PLATE ASSEMBLY

BACKGROUND OF THE INVENTION

This invention relates to apparatus employed in gel slab electrophoresis. In particular, this invention relates to a device for holding together a sandwich-type gel slab plate assembly.

Gel electrophoresis is a widely used and highly effective technique for separating complex mixtures of chemical species. While the gels used in different types of electrophoresis apparatus may vary in shape, a common gel configuration is that of a thin flat slab. Gel slabs offer many advantages, including ease of evaluation by various quantitative techniques, ease of drying and printing by autoradiography and other contact print methods, a geometry which permits improved heat dissipation and thus the opportunity for high voltage gradients, and the ability to perform simultaneous separations on a number of samples.

In many applications, the slab is most conveniently cast in a sandwich-type arrangement between two flat glass plates. Clear glass plates permit monitoring of the gel-forming solution as it is injected into the space between the plates, as well as monitoring of the finished slab and other adjacent portions of the entire apparatus while electrophoreis is taking place. The separation between the plate is typically maintained by spacer strips along the opposing vertical side edges. The entire assembly is held together by a clamp at each vertical edge. While the pressure exerted by the clamps must be tight enough to insure a seal, it is frequently difficult to provide a pressure which is sufficiently even and controllable to reduce the danger of breakage of the glass.

Prior art efforts known to the inventors which have addressed the same or related problems, consists of U.S. Pat. No. 4,518,476 (1985) to Delony entitled End Clamp for Gel Slab Plate Assembly; and U.S. Pat. No. 4,560,459 (1985) to Hoefer, entitled Vertical Gel Sandwich for use in electrophoresis and method therefor. The prior art as represented by the above, does not offer the convenience and safety that our invention, as set forth below, does.

SUMMARY OF THE INVENTION

The present invention pertains to an end clamp means for use with a gel slap plate assembly, such assembly including a pair of flat, rectilinear plates separated at longitudinal end surfaces thereof by spacers. The invention end clamp means more particularly comprises an elongate wedge element have a longitudinal dimensional of said pair of flat plates. The wedge, in transverse cross-section, substantially defined a scalene triangle having a major base, a minor base and a hypotenuse. Said major base is adapted for flush press-fit contact with a flat end of said pair of rectilinear plates. Further provided is a substantially U-shaped clamp housing proportioned to longitudinally surround, on three sides, one longitudinal edge of said pair of plates. Said housing is provided, upon its plate edge surrounding surface, with an inclined plane proportioned to mate with said hypotenuse of said wedge element. Yet further provided is means for slectively moving said hypotenuse of said wedge element along said inclined plane of said clamp housing. Said moving means comprises knob and thread menas for mechanically coupling said wedge through its minor base, to said clamp housing through an analog range of linear motion including, at one boundary condition thereof, a press-fit flush contact of said major base against said longitudinal end of said pair of plates. Thereby, a uniform pressure of said major base of said wedge element against said plate edge may be obtained by the advancing of said knob and thread means.

It is accordingly an object of the present invention to provide an end clamp for a sandwich-type gel slab assembly adapted to avoid localized stresses on the plate and to provide a large degree of control to the operator.

The above and yet other objects and advantages of the present invention will become apparent from the hereinafter set forth Detailed Description of the Invention, the Drawings, and Claims appended herewith.

DETAILED DESCRIPTION OF THE INVENTION

Figure 1:
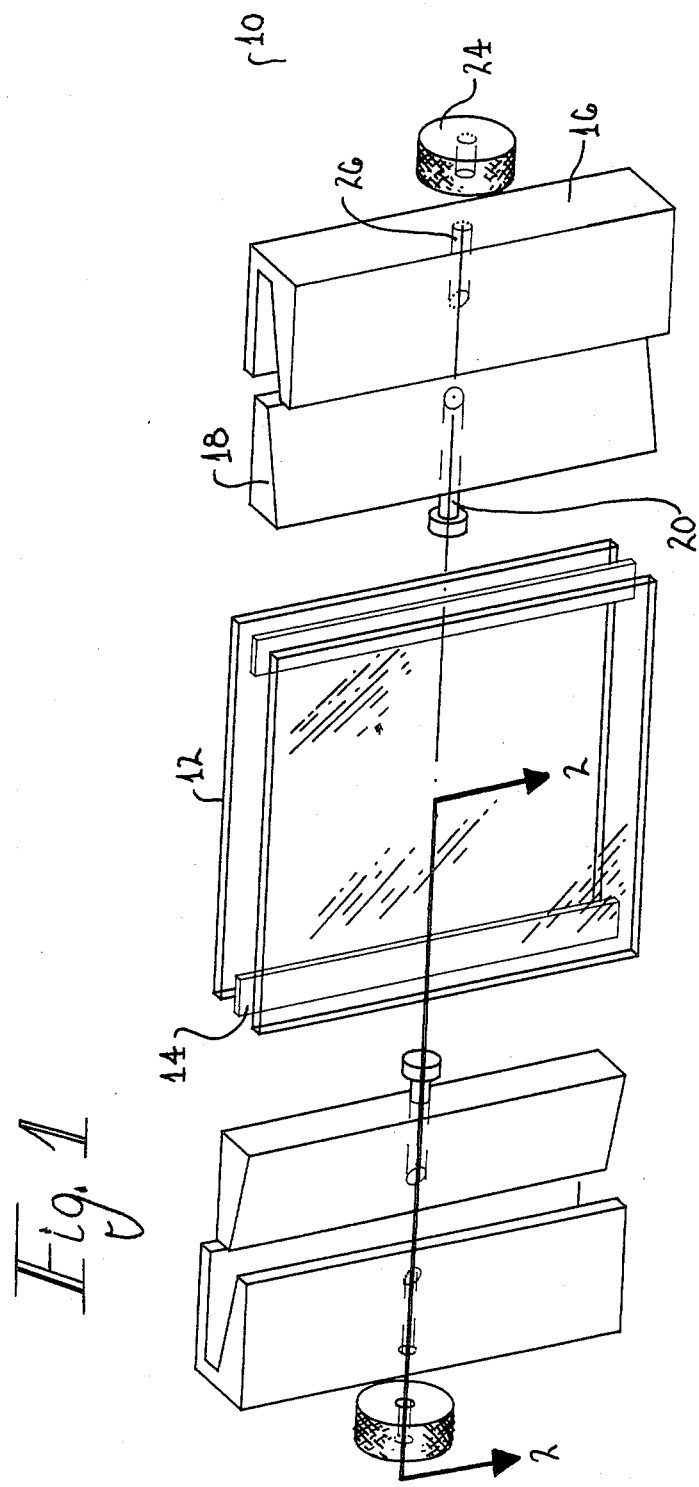
FIG. 1 is an exploded perspective view of the inventive end clamp assembly and associated gel slab plate assembly.

In the exploded view of FIG. 1 there is shown at the center thereof, a typical prior art gel slab plate assembly that includes a pair of glass plates 12 separated by spacers 14. The requirement, as above set forth in the Background of the Invention, is to maintain said plates 12 in a condition such that the pressure of any medium placed therebetween will be substantially uniform and such that the plates themselves will avoid localized stresses and pressures and further to maintain a fluid-tight longitudinal seal at the edges of said plates 12.

Figure 2:
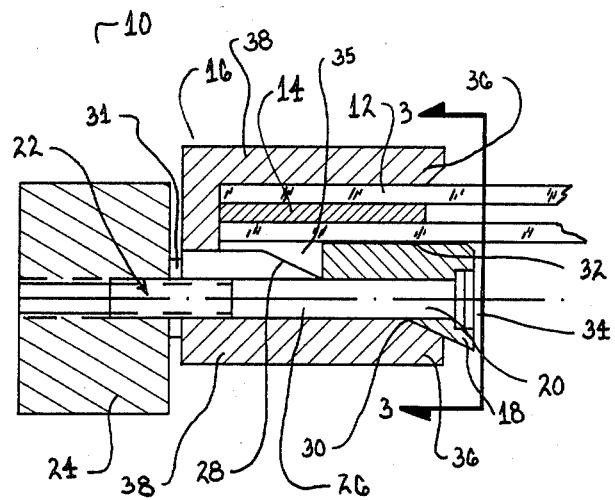
FIG. 2 is a axial cross-sectional view taken through line 2—2 of FIG. 1.

The inventive end clamp assembly 10 is shown both on the left and right sides of the view of FIG. 1. Said end clamp assembly, more particularly, includes a U-shaped clamp housing 16 which, as may be seen in the cross-sectional view of FIG. 2, is proportioned to surround, on three sides, said plate 12. Included on the plate-surrounding the surface of clamp housing 16 is an inclined plane 28 (later described in further detail).

Also shown in said FIGS. 1 and 2 is a clamp wedge 18 having, in transverse cross-section, the geometry of a scalene trinagle, this more particuarly including a hypotenuse 30, a major base 32 and a minor base 34. Said hypotenuse 30 is adapted for flush slideable engagement with plane 28 of said clamp housing 16.

There is further provided means for selectively moving said hypotenuse 30 of said wedge element 18 along said inclined plane 28 of said clamp housing 16. Said selective moving means more particualrly comprises knob and thread means in the form of a tightened bolt 20 secured at minor base 34 of clamp wedge 18 and extending in a direction parallel to that of major base 32 of the clamp wedge into inclined surface 28 of clamp housing 16 and extending outward therefrom. The entire length of tightening bolt 20 is provided with threading 22 which meets with the interior threading of knob 24. The turning of knob 24 and thereby of threaded bolt 26, thru a slotted hole of clamp housing 16 constitute an integral mechanical means for the coupling of said clamp wedge 18 to said clamp housing 16 and, through the selective rotation or knob 24, the movement of wedge element 18 along its hypotenuse, upon inclined surface 28, upwardly (with reference to the illustration of Fig.2) in the direction of glass plates 12. That is, through the rotation of knob 24, clamp wedge 17 will be moved diagonally upward through an analog range of linear motion including, at one boundary condition thereof, the press-fit contact of said major base 32 against a longitudinal end of said pair of glass plates 12.

It has been found that this method provides a convenient means by which a uniform pressure may be applied and a reliable fluid seal obtained across the longitudinal dimension of the edge of a gel slab plate assembly. Conversely, wedge element 18 may be easily released by simply reversing the direction of rotation of knob 24.

It is to be noted that the acute subtended angle defined by the virtual intersection of hypotenuse 30 and major base 32 of wedge element 28 may, in one embodiment, exceed the subtended angle 35 of the virtual intersection of plane 28 and the outer surface of plate 12 by between one and three degrees. This refinement of the present structure is to necessary to offset the greater angular displacement that occurs at the sandwich side ends 36 of the jaws of clamp housing 16 as compared to that which occurs at the knob side ends 38 of said jaws.

Figure 3:
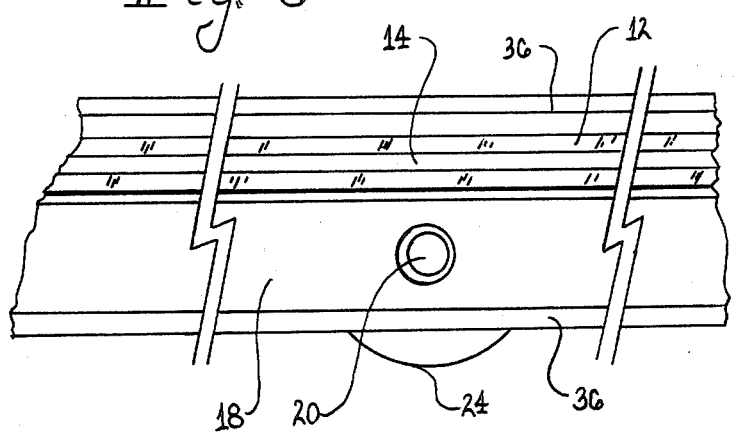
FIG. 3 is a schematic end axial view taken along line 3—3 of FIG. 2.

It is noted that FIG. 3 also shows the use of washer 31 surrounding bolt 20.

From the above described use of a simple inclined plane with a bolt and thread means, an effective and convenient gel slab end clamp means is obtained, whereas, in the prior art, mechanical structures of substantial complexity as for example, are illustrated in said U.S. Pat. No. 4,518,476, referenced in the Background of the Invention, are required to achieve the same function.

Accordingly, while there has been shown and described the preferred embodiment of the present invention, it will be understood that the invention may be embodied otherwise than as herein specifically illustrated or described and that within said embodiments certain changes in the detail and construction, and the form of arrangement of the parts may be made without departing from the underlying idea of principles of this invention within the scope of the appended claims.

Having thus described our invention, what we claim as new, useful and non-obvious and, accordingly, secure by Letters Patent of the United States is:

1. An end clamp means for a gel slab plate assembly, said assembly including a pair of flat, rectilinear plates separating at longitudinal ends thereof by spacers, in which said clamp means comprises:
    (a) an elongate wedge element having a longitudinal dimension substantially equal to the longitudinal dimension of said pair of plates, said wedge, in transverse cross-section, substantially defining a scalene triangle having a major base, a minor base, and a hypotenuse, said major base thereof adapted for flush press-fit contact with a longitudinal end of said pair of rectilinear plates;
    (b) a substantially U-shaped clamp housing proportioned to longitudinally surround, on three sides, one longitudinal edge of said pair of plates, said housing having, on said plate surrounding surface thereof, an inclined plane proportional to mate with said hypotenuse of said wedge element;
    (c) means for selectively moving said hypotenuse of said wedge element along said inclined plane of said clamp housing through an analog range of linear motion including, at a boundary condition thereof, a press-fit contact of said major base of said clamp wedge against the longitudinal edge of said pair of plates, whereby a uniform pressure of said major base of said wedge element against the plate edge may be conveniently and safely obtained by the selective advance of said moving means.

2. The end clamp means as recited in claim 1 in which said selective moving means comprise knob and thread means mechanically coupling said wedge element, through its minor base, through the use of a bolt passing rotationally through said clamp housing and terminating in a knob means by which said wedge element may be caused to selectively hold and secure said wedge element against said inclined plane of said clamp housing and, concurrently, against the logitudinal end of said glass plates.

* * * * *